United States Patent
Weber

(10) Patent No.: US 8,591,523 B2
(45) Date of Patent: Nov. 26, 2013

(54) MID-POINT LOCK SUTURE CUTTER

(75) Inventor: Robert M. Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 669 days.

(21) Appl. No.: 12/029,982

(22) Filed: Feb. 12, 2008

(65) Prior Publication Data

US 2008/0195129 A1    Aug. 14, 2008

Related U.S. Application Data

(60) Provisional application No. 60/900,992, filed on Feb. 13, 2007.

(51) Int. Cl.
*A61B 17/10* (2006.01)

(52) U.S. Cl.
USPC .......................................................... 606/138

(58) Field of Classification Search
None
See application file for complete search history.

(56) References Cited

U.S. PATENT DOCUMENTS

| | | | |
|---|---|---|---|
| 5,174,300 A * | 12/1992 | Bales et al. .................. | 600/564 |
| 5,235,966 A * | 8/1993 | Jamner .......................... | 600/204 |
| 5,250,056 A * | 10/1993 | Hasson .......................... | 606/151 |
| 5,286,255 A * | 2/1994 | Weber .............................. | 604/22 |
| 5,290,308 A * | 3/1994 | Knight et al. .................. | 606/205 |
| 5,304,203 A * | 4/1994 | El-Mallawany et al. ....... | 606/207 |
| 5,308,357 A * | 5/1994 | Lichtman ....................... | 606/205 |
| 5,383,877 A * | 1/1995 | Clarke ........................... | 606/148 |
| 5,507,756 A * | 4/1996 | Hasson .......................... | 606/139 |
| 5,522,830 A * | 6/1996 | Aranyi .......................... | 606/174 |
| 5,575,805 A * | 11/1996 | Li .................................. | 606/206 |
| 5,628,758 A * | 5/1997 | Otten et al. .................... | 606/148 |
| 5,674,228 A * | 10/1997 | Henderson et al. ........... | 606/137 |
| 5,752,972 A | 5/1998 | Hoogeboom | |
| 5,792,178 A * | 8/1998 | Welch et al. .................. | 606/208 |
| 5,827,263 A | 10/1998 | Furnish et al. | |
| 5,922,007 A | 7/1999 | Hoogeboom et al. | |
| 5,928,263 A * | 7/1999 | Hoogeboom .................. | 606/205 |
| 6,635,072 B1 * | 10/2003 | Ramamurti et al. .......... | 606/208 |
| 6,638,287 B2 * | 10/2003 | Danitz et al. .................. | 606/157 |
| 6,676,676 B2 * | 1/2004 | Danitz et al. .................. | 606/157 |
| 6,685,715 B2 * | 2/2004 | Danitz et al. .................. | 606/157 |
| 6,932,825 B2 * | 8/2005 | Anderson ...................... | 606/147 |
| 7,566,334 B2 * | 7/2009 | Christian et al. ............... | 606/51 |
| 7,789,878 B2 * | 9/2010 | Dumbauld et al. ............. | 606/42 |
| 2002/0095177 A1 * | 7/2002 | Kupferschmid et al. ...... | 606/205 |

(Continued)

FOREIGN PATENT DOCUMENTS

| | | |
|---|---|---|
| CH | 659 381 A5 | 1/1987 |
| DE | 298 06 799 | 6/1998 |
| DE | 103 14 072 A1 | 10/2004 |
| DE | 20 2005 020 819 U1 | 9/2006 |

(Continued)

*Primary Examiner* — Corrine M McDermott
*Assistant Examiner* — Son Dang
(74) *Attorney, Agent, or Firm* — Dickstein Shapiro LLP

(57) ABSTRACT

A surgical suture cutter that has a "wishbone" configuration and is provided with a locking mechanism having a mid-point lock that allows two operating handles to be locked in a predetermined position at which point the cutting jaw is held flush with the shaft but suture between the jaws of the cutter is allowed to slide without being cut. The locking mechanism is formed of first and second members provided with a first engagement element (for example, a hook) and a second engagement element (for example, a notch), to allow secure engagement of the first engagement element when the suture cutter instrument is in the mid-point locked position.

8 Claims, 2 Drawing Sheets

(56) References Cited

U.S. PATENT DOCUMENTS

| | | |
|---|---|---|
| 2002/0143346 A1 | 10/2002 | McGuckin et al. |
| 2006/0206144 A1* | 9/2006 | Miersch .................. 606/205 |
| 2007/0179524 A1 | 8/2007 | Weber et al. |
| 2008/0009900 A1* | 1/2008 | Heaven et al. ............ 606/207 |
| 2008/0132915 A1* | 6/2008 | Buckman et al. .......... 606/138 |

FOREIGN PATENT DOCUMENTS

| | | |
|---|---|---|
| EP | 0 134 251 | 3/1985 |
| EP | 1 815 809 A1 | 8/2007 |
| FR | 2 566 261 | 12/1985 |
| GB | 702 683 | 1/1954 |
| WO | WO 81/03122 | 11/1981 |

* cited by examiner

MID-POINT LOCK SUTURE CUTTER

CROSS REFERENCE TO RELATED APPLICATIONS

This application claims the benefit of U.S. Provisional Application Ser. No. 60/900,992 filed on Feb. 13, 2007, the entire disclosure of which is incorporated by reference in its entirety herein.

FIELD OF THE INVENTION

The present invention relates to the field of surgery and, in particular, to a novel instrument for handling and cutting suture during endoscopic surgical procedures.

BACKGROUND OF THE INVENTION

Surgeons frequently close incisions or wounds, or otherwise join tissue portions, with a suture. After passing the suture through the tissue portions, the surgeon must tie the suture to draw the tissue portions together and prevent them from separating. When sutures are tied in a region having restricted access (such as an endoscopic work site within a patient's body), the surgeon is presented with special challenges. Typically, the knot is formed outside the patient and then is pushed towards those tissue portions to be joined together.

Once a knot has been positioned against tissue portions so that they are securely fastened together, the surgeon must cut back the ends of the suture. This procedure can be difficult when using conventional instruments such as surgical scissors, particularly where access is limited such as in endoscopic procedures where access of instruments is normally provided through one or more portals formed directly in the patient's body or through one or more cannulas inserted into the patient's body through small incisions.

Accordingly, a need exists for an improved and reliable suture cutter, whereby a surgeon can rapidly and accurately cut a suture strand and trim back the strands from a knot. A need also exists for an improved surgical cutting instrument that allows controlled manipulation of suture or other flexible strands that are employed during or in conjunction with endoscopic surgeries. A surgical suture cutter that is not only able to cut the suture, but also able to hold the suture, and be locked into that position, during insertion of the instrument through the cannula, would be desirable.

SUMMARY OF THE INVENTION

The present invention provides an improved surgical cutter which is designed to cut a suture or other flexible strand with a cutter assembly provided at the distal end of the instrument. The cutter assembly may be actuated by an actuating mechanism located on the handle of the instrument. Preferably, the handle has a "wishbone" configuration and is provided with a locking mechanism having a mid-point lock that allows two operating handles to be locked in a middle position in which the cutting jaw is held flush with the shaft but allows the suture between the jaws to slide (rather than being cut).

Other features and advantages of the present invention will become apparent from the following description of the invention, which refers to the accompanying drawings.

DETAILED DESCRIPTION OF THE PREFERRED EMBODIMENTS

Figure 1:
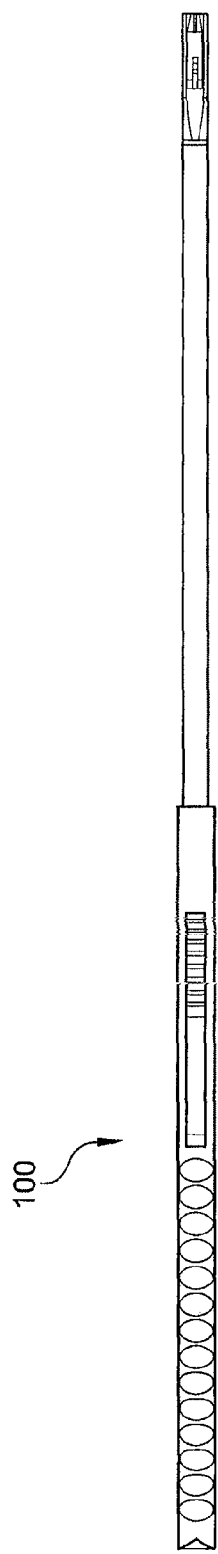
FIG. 1 illustrates a top view of a surgical cutter of the present invention.

The present invention provides a surgical cutting instrument for endoscopic surgeries which is designed to accurately cut a flexible strand, for example suture.

The present invention provides an improved surgical cutter which is designed to cut a suture or other flexible strand with a cutter assembly provided at the distal end of the instrument. The cutter assembly may be actuated by an actuating mechanism located on the handle of the instrument. Preferably, the handle has a "wishbone" configuration and is provided with a locking mechanism having a mid-point lock that allows two operating handles to be locked in a position in which the cutting jaw is held flush with the shaft but allows the suture between the jaws to slide (rather than being cut) so that the instrument can be used to slide down the suture during insertion through a cannula.

The locking mechanism is actuated by an actuating mechanism that is located on the handle and that may include, for example, a mechanical thumb lever or trigger connected to the shaft of the instrument. The mechanical thumb lever or trigger is moveable into a position in which the handle is locked, and suture between the jaws at the distal end of the instrument is free to slide, but is not cut. When the handle arms are brought together, an end effect assembly of the cutter located at the distal end of the instrument (for example cutting blades of the cutter) is maneuvered as desired to either be brought flush to the shaft to allow suture sliding (in the locked mid-point position), or to cut the suture (when the handle arms are advanced closer together). The motion of the handle arms is translated through a connecting rod to urge the blades of the surgical cutter together and to cut the flexible strand.

Referring now to the drawings, where like elements are designated by like reference numerals, FIGS. 1-4 illustrate a surgical cutting instrument 100 of the present invention provided with cutter assembly 3 located at the distal end of the instrument and actuated by a locking mechanism 11. The locking mechanism 11 is a mid-point locking mechanism located on handle 20. The surgical cutter 100 of FIGS. 1-4 may be employed in many surgical procedures, non-limiting examples including manipulating and retrieving suture, or cutting suture during surgery.

In a preferred embodiment, handle 20 (comprising grasper wishbone thumb 7 and grasper wishbone finger 10) has a "wishbone" configuration that allows the surgical cutter 100 to be easily actuated and maneuvered so that it remains stable during arthroscopy and with the orientation desired by the surgeon. The "wishbone" configuration of the handle also allows a surgeon to grip the handle ergonomically and to effectively cut suture during surgery.

Figure 2:
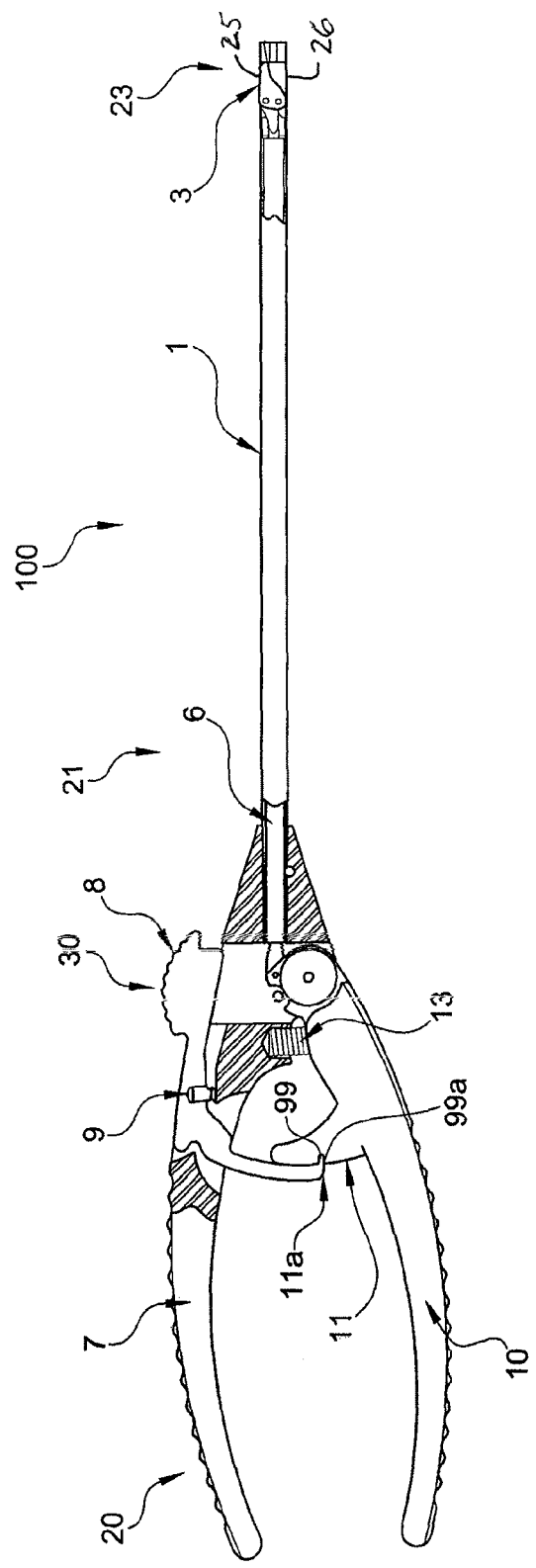
FIG. 2 illustrates a partial cross-sectional view of the instrument of FIG. 1.
Figure 3:
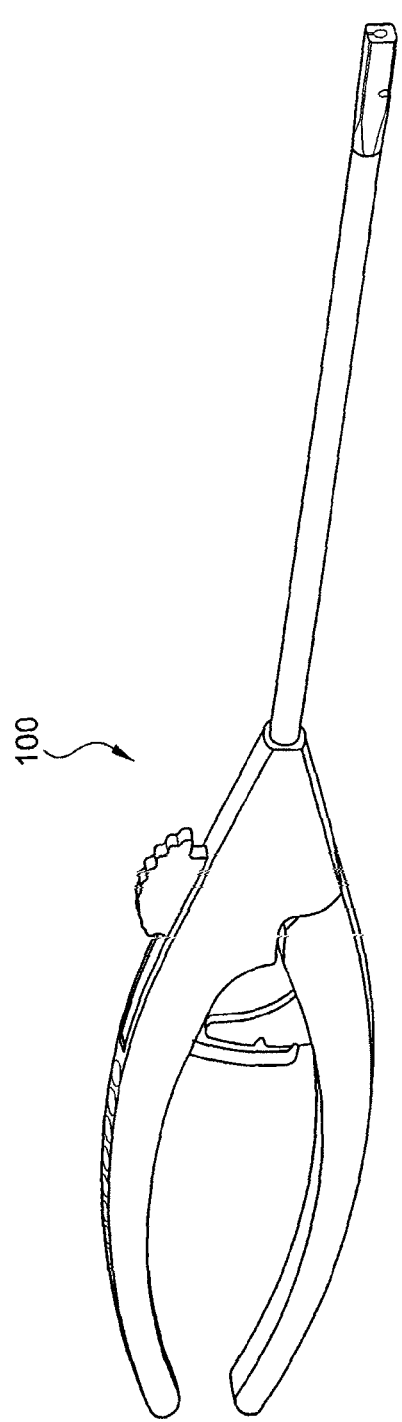
FIG. 3 illustrates a perspective view of the instrument of FIG. 1.
Figure 4:
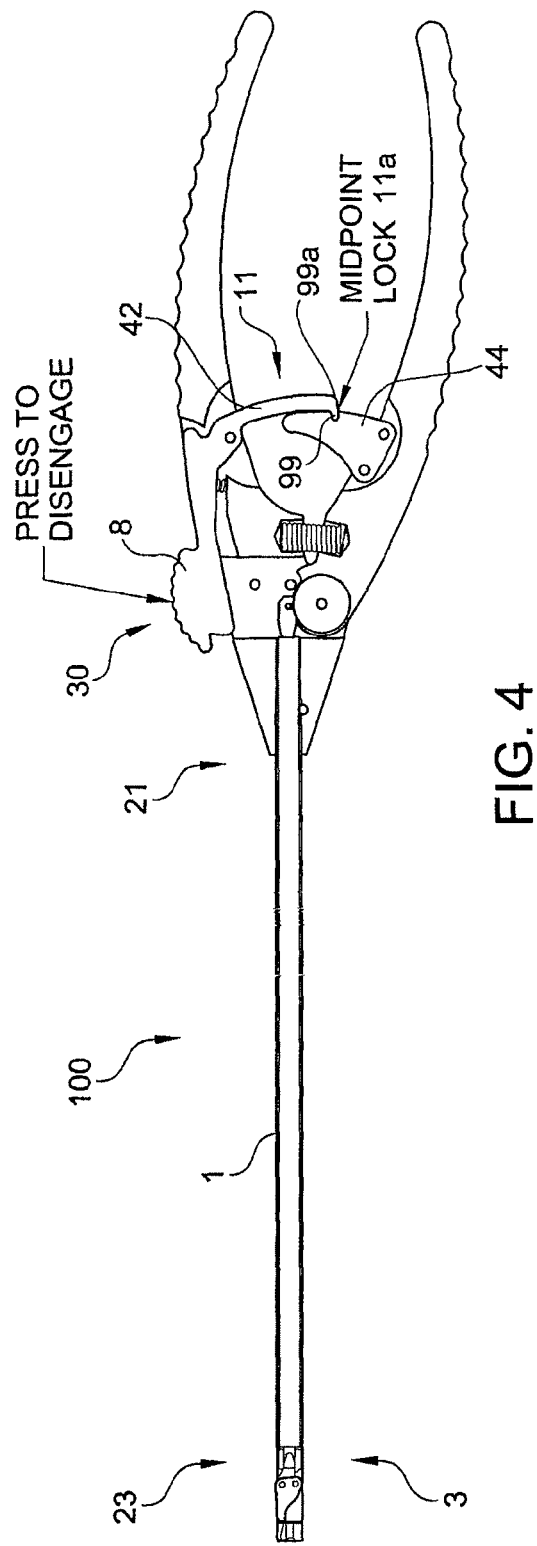
FIG. 4 illustrates another partial cross-sectional view of the instrument of FIG. 1.

As shown in FIGS. 2 and 4, the handle of the present invention is provided with a locking mechanism 11 that allows two operating handles having a "wishbone" configuration in a plier-type arrangement to be locked in a predetermined mid-point position, in which the cutting jaw is held flush with the shaft but allows the suture to slide, or allows the jaws to move relative to each other, when the lock is released.

As illustrated in FIGS. 1-4, the surgical cutter 100 includes handle 20, a shaft 1 having a proximal end 21 and a distal end 23, and an actuating mechanism 30 located on the handle and in communication with the ratchet mechanism 11. The handle is mechanically connected to the distal tip 23 of the instrument and, when actuated, actuates cutter assembly 3. In an exemplary embodiment, the cutter assembly 3 may comprise a pair of cutting blades 25, 26 that hold and cut suture by pivoting between an open or closed position.

FIGS. 2 and 4 illustrate in more detail the actuating mechanism 30 and the ratchet mechanism 11 which are part of handle 20 of the present invention. The actuating mechanism 30 comprises a mechanical thumb lever or trigger 8 provided with a ratchet spring 9. Locking mechanism 11 comprises a first member 42 in communication with a second member 44. In the "locked" position illustrated in FIGS. 2 and 4, first member 42 locks into about the middle of the second member 44 (at mid-point lock or mid-point position 11 a), at which point the handles are in a position in which the blades of cutter 3 and 23 are relatively flush but provide enough space between them to allow sutures to slide, and not be cut, at the distal end of the instrument. FIG. 4 illustrates suture 60 in the space between the blades of cutter 3 and 23, at the distal end of the instrument. Suture 60 can slide but is not cut when the instrument is in the "locked" position.

When the lock is released, which occurs automatically when the arms of the handle are brought together, the handles 7 and 10 are then free to move relative to each other (biased apart by spring 13), thus closing or opening the cutting blades of the suture cutter instrument to cut or open the jaws for suture loading, respectively.

In an exemplary embodiment, one of the first and second members 42, 44 may be provided with a first engagement element 99 (for example, a hook or protuberance 99) while the other of the first and second members 42, 44 may be provided with a second engagement element 99a (for example a corresponding notch 99a), to allow secure engagement of the first engagement element when the suture cutter instrument is in the mid-point locking position 11a. Preferably, the second engagement element 99a (for example, the notch 99a of member 44) is located at about the middle of the most proximal edge of the second member 44, in proper position to allow the cutting blades 3 and 23 to be positioned relatively flush with each other but provide space for suture sliding.

The hook 99 and notch 99a of the locking mechanism are shaped such that simply squeezing the arms of the handle together causes the hook 99 to come out of the notch 99a, releasing the lock. The arms of the handle are now free to move relative to each other, such that further squeezing of the arms by the user causes corresponding relative movement of the blades of the cutter 3 at the distal end of the instrument together (through longitudinal movement of inner tube 6 within outer tube 1), cutting the suture.

In use, the handle 20 of the instrument 100 is held across the palm of a user's hand in a manner similar to a pair of pliers. Advantageously, the instrument 100 can be held in the user's palm with the distal tip pointing away from the body, or reversed in the palm with distal tip pointing toward the body, affording the user greater flexibility in certain surgical situations. The user can grip the handle and trigger in one hand without the need for a finger ring or a thumb ring on the handle of the instrument 100. The actuating mechanism is positioned for easy manipulation by the user's thumb simply by pushing down.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed is:

1. A surgical suture cutting instrument, comprising:
   a shaft;
   an articulating suture cutting mechanism disposed at the distal end of the shaft, the articulating cutting mechanism comprising a pair of cutting blades for holding and cutting sutures;
   a suture disposed within the articulating cutting mechanism;
   a handle extending from the shaft, the handle being provided with arms and a locking mechanism, the locking mechanism being manipulable by a user between a locked position and an unlocked position, and with a ratchet comprising a first member in communication with a second member, wherein the first member is provided with a first engagement element and the second member is provided with a second engagement element, the second engagement: element being located at about a mid point of the second member such that the handle can be locked in a predetermined locked mid point position, causing the articulating suture cutting mechanism to be disposed at a locked mid point position, wherein the locking mechanism, when in the locked position, holds the pair of cutting blades flush with the shaft but with space between them to allow the suture disposed within the cutting mechanism to be free to slide and not to be cut, and wherein, when the locking mechanism is released and the mechanism is in the unlocked position, which occurs automatically when the arms of the handle are brought together, the arms of the handle are free to move relative to each other, biased apart by a spring, to close or open the cutting blades to cut suture or open the jaws for suture loading, respectively; an actuating mechanism located on the handle, the actuating mechanism being movable into the predetermined locked mid point position in which an engagement element of one member fits into a notch of another member located at a predetermined position such that the handle is locked at the locked midpoint position and the suture disposed within the cutting mechanism is free to slide and not to be cut; and
   an actuating mechanism located on the handle, the actuating mechanism being movable into the predetermined locked mid point position in which an engagement element of one member fits into a notch of another member located at a predetermined position such that the handle is locked at the locked midpoint position and the suture disposed within the cutting mechanism is free to slide and not to be cut; and
   a rod or tube extending through the shaft and linking the articulating suture cutting mechanism to the handle.

2. The surgical suture cutting instrument of claim 1, wherein the handle extends longitudinally from the shaft.

3. The surgical suture cutting instrument of claim 1, wherein the first engagement element is a hook and the second engagement element is a notch.

4. The surgical suture cutting instrument of claim 1, wherein the actuating mechanism is adapted to be manipulated by a single digit.

5. The surgical cutting instrument of claim 1, wherein the instrument is an arthroscopic suture cutting instrument.

6. An arthroscopic suture cutting instrument, comprising:
a shaft;
an articulating suture cutting mechanism disposed at a distal end of the shaft the articulating cutting mechanism comprising a pair of cutting blades for holding and cutting sutures;
a suture disposed within the articulating cutting mechanism;
a multi-member, pliers-like grip disposed at a proximal end of the shaft, the grip having a wishbone configuration and including:
a handle extending from the shaft and provided with arms and a locking mechanism, the locking mechanism comprising a first member in communication with a second member, wherein the first member is provided with a hook and the second member is provided with a notch, the notch being located at about a mid point of the second member, the locking mechanism being manipulable by a user between a locked position and an unlocked position, such that the handle can be locked in an intermediate position in which the hook engages the notch, causing the articulating suture cutting mechanism to be disposed at an intermediate predetermined locked, mid point position at which the pair of cutting blades are flush with the shaft but with space between them to allow the suture disposed within the cutting mechanism to be free to slide and not to be cut, and wherein, when the locking mechanism is released and the mechanism is in the unlocked position, which occurs automatically when the arms of the handle are brought together, the arms of the handle are free to move relative to each other, biased apart by a spring, to close or open the cutting blades to cut suture or open the jaws for suture loading, respectively; and
a rod or tube extending through the shaft and linking the articulating suture cutting mechanism to the handle.

7. The arthroscopic suture cutting instrument of claim 6, wherein the handle comprises a first handle member and a second handle member which are substantially symmetric across a longitudinal axis of the instrument when the locking mechanism is actuated into a mid point lock position.

8. The arthroscopic suture cutting instrument of claim 7, wherein the first handle member and the second handle member are adapted to be locked into position relative to each other by the locking mechanism.

* * * * *